United States Patent [19]

Flygare et al.

[11] 4,369,404

[45] Jan. 18, 1983

[54] METHOD AND APPARATUS FOR THE SPECTROSCOPIC OBSERVATION OF PARTICLES

[76] Inventors: Willis H. Flygare, 112 W. Pennsylvania, Urbana, Ill. 61801; Terrill J. Balle, 2292 A Aster Rd., Bethlehem, Pa. 18108

[21] Appl. No.: 187,145

[22] Filed: Sep. 15, 1980

[51] Int. Cl.³ ............................................. G01R 27/04
[52] U.S. Cl. ................................................ 324/58.5 C
[58] Field of Search ...................... 324/58.5 C, 58.5 R, 324/58.5 A, 316

[56] References Cited

U.S. PATENT DOCUMENTS 2,670,649  3/1954  Robinson ................. 324/58.5 A X
2,882,493  4/1959  Dicke ............................ 324/58.5 C
3,798,532  3/1974  Hausser ............................. 324/316
4,110,686  8/1978  Leskovar et al. ............. 324/58.5 C Primary Examiner—Stanley T. Krawczewicz
Attorney, Agent, or Firm—Merriam, Marshall & Bicknell

[57] ABSTRACT

A method and apparatus for the spectroscopic observation of particles, such as molecules, transient molecules or atoms, molecular complexes, etc., including a Fabry-Perot cavity having a resonant frequency, a source of pulsed particles to be investigated, such as a pulsed supersonic nozzle beam applied to the cavity, while simultaneously applying a radiation pulse to the cavity sufficient to polarize the particles and provide a coherent radiation emission over a frequency band centered at the cavity resonant frequency, and observing the coherent emission frequencies which are characteristic of the respective particles within the pulsed particles applied to the cavity.

12 Claims, 1 Drawing Figure

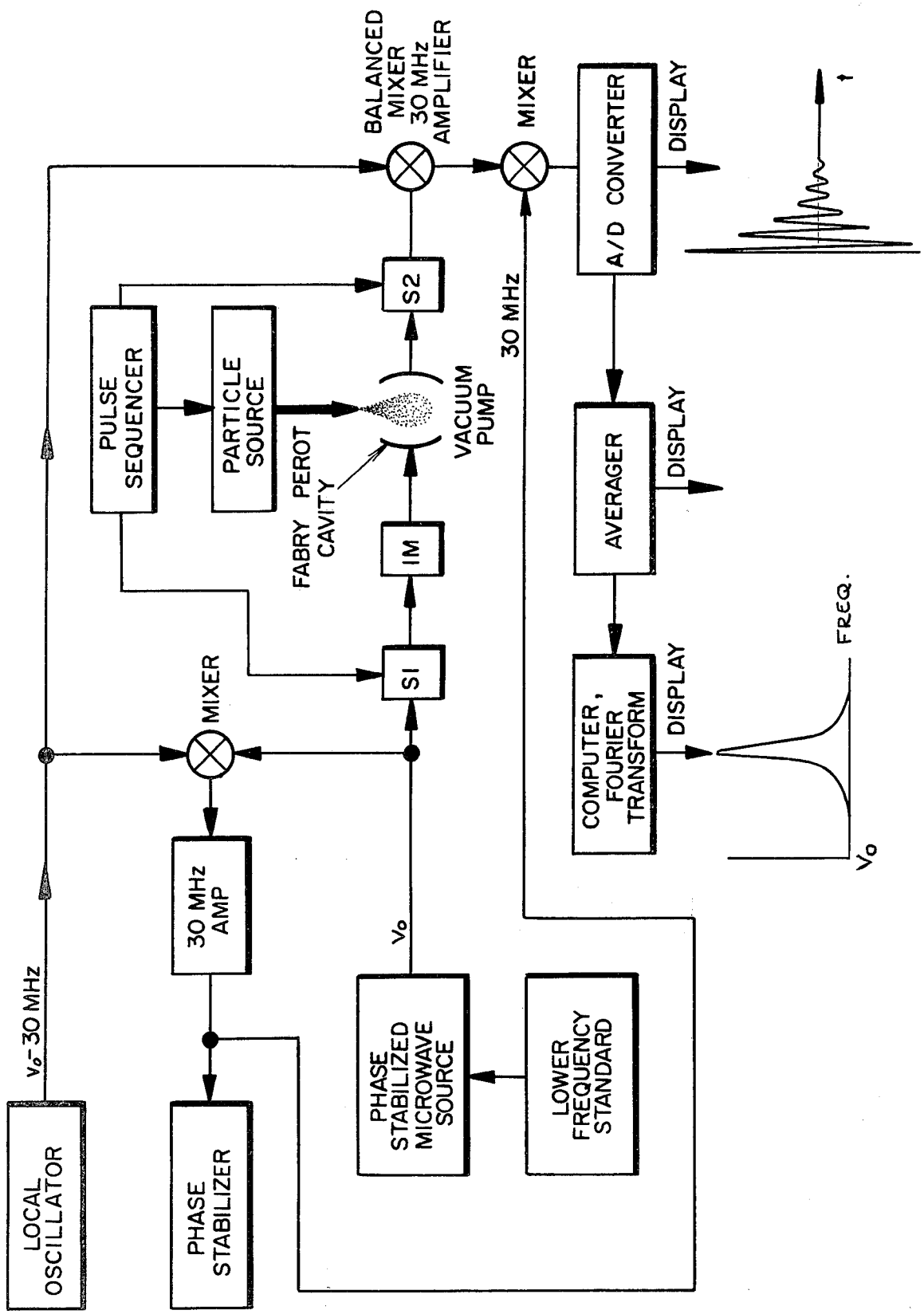

METHOD AND APPARATUS FOR THE SPECTROSCOPIC OBSERVATION OF PARTICLES

This invention relates to spectroscopy, and in particular a method and apparatus for the spectroscopic observation of particles, such as molecules, transient molecules or atoms, molecular complexes, etc.

A published article of interest is in the *Journal of Chemical Physics* 71(6), Sept. 15, 1979, page 2723, entitled "*A New Method For Observing The Rotational Spectra of Weak Molecular Complexes*: KrH Cl", T. J. Balle, E. J. Campbell, M. R. Keenan, and W. H. Flygare, and reference may be made to the listed published articles therein for background to the present invention.

The present invention is directed to the interaction of a pulsed source of particles with a radiation pulse, and wherein either the perturbed particles or the subsequent reemission of radiant energy of the particles can be observed. A Fabry-Perot cavity is utilized as the pulsed particles radiation pulse interacting medium. The subsequent coherent emission of the particles is detected and observed. This technique enables the observation of the spectra of particles, such as molecules, transient molecules or atoms, and molecular complexes.

In accordance with the principles of the present invention, there is provided a Fabry-Perot cavity having a cavity resonant frequency; a source of pulsed particles to be investigated, such as a pulsed supersonic nozzle beam of a gas or gas mixture used to generate a very low temperature gaseous sample, applied to the cavity; while simultaneously applying a radiation pulse to the Fabry-Perot cavity sufficient to polarize the particles and provide coherent radiation emission from the polarization over a frequency band centered at the cavity resonant frequency; and finally, observing the coherent emission frequencies which are characteristic of the respective particles within the pulsed particles applied to the cavity.

The embodiment described herein is in the microwave frequency so that the well-known Fourier transform technique or time domain method can be utilized, although it is to be understood that any type of electromagnetic radiation that can be pulsed, such as a laser, is suitable.

In the drawing, FIG. 1 is a block diagram illustrating an embodiment of the invention in the microwave frequency range. Particles, such as molecules, applied as a pulse to a Fabry-Perot cavity interact with a microwave pulse to obtain emitted radiation which is characteristic of the molecules. The emitted radiation is detected and observed to obtain the respective molecular characteristics.

Referring now to FIG. 1, a microwave oscillator at frequency $v_o$ is phase stabilized to a harmonic of a lower frequency oscillator which is monitored with a frequency counter. The primary microwave oscillator at $v_o$ is then used to phase stabilize the local oscillator at a frequency of $v_o - 30$ MHz; this second oscillator is used in the subsequent superheterodyne detection of the signal. The primary microwave source at $v_o$ is then formed into a radiation pulse by the pulse sequencer enabling of the first switch, S1. The radiation pulse is impedance matched (IM) to the Fabry-Perot cavity. The pulse sequencer also simultaneously activates a source of pulsed particles, which particles are applied in the form of a nozzle beam to the cavity. The pulse sequencer ensures that the microwave radiation pulse is applied to the cavity simulataneously with the pulsed particles so as to interact therewith. The second switch, S2, under control of the pulse sequencer, blocks the microwave source pulse from the balanced mixer until the microwave pulse has dissipated.

The relaxation time of the Fabry-Perot cavity, or the time necessary to charge or discharge the microwave energy to $e^{-1}$ of its steady state value is given by $t_c = Q/2\pi v_c$ where Q is the normal quality factor for the cavity and $v_c$ is the cavity resonant frequency. Typical values of $v_c = 10^{10}$ Hz and $Q = 10^4$ given $t_c \approx 0.16$ μs which gives a cavity frequency response with full-width at half-power of $\Delta v_c 32\ 1/(2\pi t_c) = 1$ MHz.

The microwave pulse width, $t_p$, must exceed $t_c$ in order to reach a steady state power in the cavity. If $t_p >> t_c$, it is easy to polarize a band of molecular frequencies, $\Delta v_p$, up to $\Delta v_c$ centered at a microwave frequency , $v_o$, which coincides with the cavity resonance frequency. Maximum polarization of the gas is achieved following a $\pi/2$ pulse, $T_2 >> t_p$, where $T_2$ is the polarization relaxation time which is related to the low power steady state molecular transition half width at half height by $\Delta v = 1/(2\pi T_2)$. Alternatively, the radiation frequency could be swept across the resonant frequency to cause the polarization.

Following polarization of a band of molecular frequencies $\Delta v_p \leq \Delta v_c$ centered at $v_o$, the microwave pulse is switched off and it dissipates with a relaxation time, $t_c$. We now require the molecules to maintain their coherent polarization for a period of time long relative to $t_c$; $T_2 >> t_c$. Typical $\Delta v$ values range from 3-7 kHz, giving $T_2 \approx 32$ μs which clearly satisfies $T_2 >> t_c = 0.16$ μs from our previous example where $Q = 10^4$ and $v_c = 10^{10}$ HZ. The $T_2 >> t_c$ requirement allows the original microwave pulse to die away before the coherent polarization is lost. After the microwave pulse has died away, switch S2 is enabled by the pulse sequencer, and the coherent emission from all polarized transitions ($\Delta v_p$) is observed in the illustrated superheterodyn receiver as a beat between the local oscillator field with the field from the coherent emission. The illustrated exponentially decaying (with $T_2$) cosine is then amplified, digitized (A/D converter), averaged, and Fourier transformed utilizing well-known techniques and commercially available components to give the emission frequency spectrum illustrated as an example.

In a constructed embodiment of the invention the source of pulsed particles is obtained from a high pressure gas chamber with the gases passing through a nozzle of about 0.5 mm diameter. A solenoid valve connected intermediate between the gas chamber and the nozzle is actuated by the pulse sequencer so that the molecular sample is applied to the Fabry-Perot cavity in the form of a pulsed supersonic nozzle beam. The sample is a mixture of gases held at pressures from less than one atmosphere to tens of atmospheres.

The gas dynamics of a continuous adiabatic expansion of a gas (or gas mixture) into a vacuum is now fairly well understood. For non-condensibles like rare gas atoms, nitrogen, oxygen, or air, the adiabatic expansion cools the gas to temperatures from 1–10 degrees Kelvin. A molecule of interest can be mixed with the noncondensible gas to obtain very low temperatures. In the case of a mixture of gases A and B, three-body collisions will form AB molecular complexes. The development of pulsed nozzle beams allows the use of higher pressures and enables the molecular complex (AB) number density to exceed by several orders of magnitude the corresponding complex number density in a continuous nozzle expansion for the same pumping speeds in the vacuum chamber.

There is a second advantage to pulsing the sample gas into the cavity. If N particles can be pumped through the cavity during a long time $t_1$ and if $t_1 >> T_2$, the number of radiation polarizing pulses, p, (pulse time $t_p$) that ca be effectively used over time $t_1$ is $p \approx t_1/3T_2$ where we as before estimate $t_p >> T_2$. If the gas flows continuously through the cavity, the observed signal to noise ratio (S/N), for period of time $t_1$, will be proportional to N divided by the square root of p. However, if now all N particles are pulsed into the cavity allowing only a single polarizing pulse during the time period $t_1$, the S/N will be proportional to N, assuming identical $T_2$ for both experiments.

The pulsed gas adiabatically expands and traverses through the Fabry-Perot cavity having a cold gas transit time of about 100 $\mu$s–1 ms through the region where the microwave field will pass at right angles. The microwave radiation pulses commence shortly after the application of the nozzle pulse and the repeating transient coherent emissions are digitized and averaged. The gas is then pumped out and one may record an equal number of microwave pulses in the empty cavity and subtract this signal (noise) from the averaged signal with the gas present.

Applications of the technique described herein could include the following:

1. The observation of trace impurities in an atmospheric or higher pressure gas. This method and apparatus is well suited to sample (through a pulsed nozzle) high pressure gas which has trace impurities. The signal intensity of the trace impurities spectra is enhanced by the adiabatic cooling in the pulsed nozzle.

2. In some cases, the trace gas in an atmospheric sample may also be observed as a complex with the components in the air, either nitrogen or oxygen.

3. If the nozzle is placed parallel to the input-output radiation axis, extremely long time coherent emission is observed. Therefore, this device may also be usable as a frequency standard.

4. Various transient species such as ions and free radicals can be produced by crossing the nozzle beam output with an electron beam, photon beam, microwave discharge or another molecular nozzle beam.

5. The pulsed valve can be replaced by a pulsed explosion chamber to study nascent species.

The foregoing detailed description has been given for clearness of understanding only, and no unnecessary limitations should be understood therefrom, as modifications will be obvious to those skilled in the art.

What is claimed is:

1. A method of spectroscopic observation of particles, such as molecules, atoms or molecular complexes, said method comprising:
   providing a Fabry-Perot cavity having a cavity resonant frequency;
   applying a source of pulsed particles to be investigated to said Fabry-Perot cavity, while;
   simultaneously applying a radiation pulse to the pulsed particles in said Fabry-Perot cavity sufficient to polarize said particles and provide coherent radiation emission frequencies from said polarization over a frequency band centered at said cavity resonant frequency;
   said coherent radiation emission frequencies characteristic of the respective particles within said source of pulsed particles applied to the Fabry-Perot cavity; and
   observing said coherent radiation emission frequencies so as to determine said respective particle characteristics.

2. The method of claim 1, wherein said observing of said coherent radiation emission frequencies is initiated after a predetermined delay time interval following the application of said radiation pulse to the pulsed particles.

3. The method of claim 2, wherein said predetermined delay time interval corresponds sustantially to a time interval greater than the duration of said radiation pulse.

4. The method of claim 1, wherein said observing of said coherent radiation emission frequencies includes the step of performing a Fourier transform.

5. The method of claim 1, including the step of impedance matching said radiation pulse to the Fabry-Perot cavity.

6. Apparatus for the spectroscopic observation of particles, such as molecules, atoms or molecular complexes, said apparatus comprising:
   a Fabry-Perot cavity having a cavity resonant frequency;
   a source of pulsed particles to be investigated;
   means for supplying a radiation pulse;
   means for simultaneously applying said pulsed particles, and said radiation pulse to said Fabry-Perot cavity sufficient to polarize said particles and provide coherent radiation emission frequencies from said polarization over a frequency band centered at said cavity resonant frequency;
   said coherent radiation emission frequencies characteristic of the respective particles within said source of pulsed particles applied to the Fabry-Perot cavity; and
   detecting means coupled to said Fabry-Perot cavity for detecting said coherent radiation emission frequencies so as to determine said respective particle characteristics.

7. Apparatus according to claim 6, including means for delaying the detection of said coherent radiation emission frequencies for a predetermined time interval following the application of said radiation pulse to said Fabry-Perot cavity.

8. Apparatus according to claim 7, wherein said predetermined time interval corresponds substantially to a time interval greater than said radiation pulse.

9. Apparatus according to claim 6, including means for performing a Fourier transform on said detected coherent radiation emission frequencies.

10. Apparatus according to claim 6, including means for impedance matching said radiation pulse to said Fabry-Perot cavity.

11. Apparatus according to claim 6, including a microwave frequency source supplying said radiation pulse, and pulse sequencing means coupled to said microwave frequency source and to said source of pulsed particles for sequencing the simultaneous application of said radiation pulse and said pulsed particles to said Fabry-Perot cavity.

12. Apparatus according to claim 11, including first switch means coupled intermediate said microwave frequency source and said Fabry-Perot cavity and second switch means coupled intermediate said Fabry-Perot cavity and said detecting means, said first and second switch means operable by said pulse sequencing means to sequentially enable the application of said radiation pulse to said Fabry-Perot cavity, and the coupling of said detecting means to said Fabry-Perot Cavity with respect to the application of said pulsed particles to said Fabry-Perot cavity.

* * * * *

UNITED STATES PATENT AND TRADEMARK OFFICE
CERTIFICATE OF CORRECTION

PATENT NO. : 4,369,404
DATED : January 18, 1983
INVENTOR(S) : Flygare et al.

It is certified that error appears in the above–identified patent and that said Letters Patent are hereby corrected as shown below:

Column 1, line 22, after the word "particles" insert two dashes ( -- ).

Column 2, line 14 should be "$\Delta V_c =$" not "$\Delta V_c 32$".

Column 3, line 9 should be "that can be" not "that ca".

Column 3, line 10 should be "$t_p \ll T_2$" not "$t_p \gg T2$".

Signed and Sealed this

Twenty-ninth Day of March 1983

[SEAL]

Attest:

GERALD J. MOSSINGHOFF

*Attesting Officer*     *Commissioner of Patents and Trademarks*